United States Patent [19]

Richter et al.

[11] 4,456,709

[45] Jun. 26, 1984

[54] POLYISOCYANATE MIXTURES, PROCESS FOR THEIR PRODUCTION AND THEIR USE IN THE PRODUCTION OF POLYURETHANE PLASTICS

[75] Inventors: Roland Richter; Hans Hettel, both of Cologne; Hanns P. Müller, Odenthal, all of Fed. Rep. of Germany

[73] Assignee: Bayer Aktiengesellschaft, Leverkusen, Fed. Rep. of Germany

[21] Appl. No.: 554,662

[22] Filed: Nov. 23, 1983

[30] Foreign Application Priority Data

Dec. 1, 1982 [DE] Fed. Rep. of Germany ....... 3244407

[51] Int. Cl.$^3$ ...................... C08G 18/14; C08G 18/79
[52] U.S. Cl. .................................... 521/160; 252/182; 521/902; 528/44; 528/67; 528/73
[58] Field of Search ................. 521/160, 902; 528/44, 528/67, 73; 252/182

[56] References Cited

U.S. PATENT DOCUMENTS

| | | | |
|---|---|---|---|
| 3,652,424 | 3/1972 | Jackson et al. | 252/182 |
| 3,970,600 | 7/1976 | Falkenstein et al. | 260/77.5 |
| 3,996,223 | 12/1976 | Gupta et al. | 260/248 NS |
| 4,243,756 | 1/1981 | Cenker et al. | 521/125 |
| 4,288,586 | 9/1981 | Bock et al. | 528/67 |
| 4,293,680 | 10/1981 | Mazanek et al. | 528/67 |
| 4,324,879 | 4/1982 | Bock et al. | 528/73 |
| 4,373,080 | 2/1983 | Reichmann | 521/160 |
| 4,379,905 | 4/1983 | Stemmler et al. | 528/73 |

FOREIGN PATENT DOCUMENTS 1022789   1/1958   Fed. Rep. of Germany .

Primary Examiner—H. S. Cockeram
Attorney, Agent, or Firm—Gene Harsh; Joseph C. Gil

[57] ABSTRACT

The present invention is directed to polyisocyanate mixtures which are liquid and stable in storage at room temperature and which have an NCO-content of from 36.5 to 45% by weight, consisting essentially of a mixture of from 25 to 70 parts by weight of partly trimerized 2,4-diisocyanatotoluene with from 30 to 75 parts by weight of unmodified 2,4-and/or 2,6-diisocyanatotoluene, a process for the production of these mixtures by mixing the individual components and the use of the mixtures as a synthesis component in the production of polyurethane plastics by the isocyanate-polyaddition process.

6 Claims, No Drawings

POLYISOCYANATE MIXTURES, PROCESS FOR THEIR PRODUCTION AND THEIR USE IN THE PRODUCTION OF POLYURETHANE PLASTICS

BACKGROUND OF THE INVENTION

This invention relates to new isocyanurate-group-containing polyisocyanates based on polyisocyanate mixtures containing 2,4-diisocyanatotoluene which are liquid and storable at room temperature, to a process for their production and to their use as a synthesis component in the production of polyurethane plastics by the isocyanate polyaddition process.

Isocyanurate-modified diisocyanatotoluenes and their use for the production of polyurethane plastics are already known in principle [cf. for example DE-OS No. 22 21 811, DE-OS No. 24 52 532 (corresponding to U.S. Pat. No. 3,996,223), DE-OS No. 24 03 858 (corresponding to U.S. Pat. No. 3,970,600), DE-OS No. 20 63 731, DE-AS No. 10 22 789, U.S. Pat. No. 4,243,765 (Example 5) or U.S. Pat. No. 3,652,424].

The isocyanurate-modified polyisocyanate mixtures based on diisocyanatotoluene and, more particularly, on a technical 80:20-mixture of 2,4- and 2,6-diisocyanatotoluene which are specifically described in these prior publications are attended by the disadvantage that either they are not homogeneous liquids which can be stored at room temperature or, to guarantee that property, contain considerable quantities of stabilizing additives. Stabilizing additives of the type in question here are, for example, urethane- and/or allophanate-modified polyisocyanates of the type obtained in situ by modifying the polyisocyanates with polyols before or after the trimerization reaction. Other stabilizing agents are, for example, the compounds containing amide and/or acyl urea groups as described in U.S. Pat. No. 3,970,600. One feature common to these stabilizing additives is that they contain active hydrogen atoms attached to nitrogen which show a relatively pronounced tendency to react with isocyanate groups. Accordingly, although mixtures containing the above-mentioned additives often show adequate stability in storage, they lack stability in regard to their NCO-content because uncontrollable secondary reactions between the isocyanate groups and the active hydrogen atoms in the additives cannot be avoided.

Pure isocyanaurate-modified polyisocyanate mixtures based on diisocyanatotoluene which are homogeneous liquids at room temperature and which show adequate stability in storage have never been known before. In the present context, adequate stability in storage is understood to mean that the polyisocyanates protected against atmospheric moisture remain liquid at temperatures in the range from 20° to 40° C. and remain free from clouding and precipitates over a period of at least 6 months. In addition, product crystallized by cooling to <0° C. must always melt completely clearly again at temperatures in the above-mentioned range.

Accordingly, the object of the present invention is to provide isocyanurate-modified polyisocyanates based on diisocyanatotoluene which are liquid and stable in storage at room temperature and which do not contain any significant quantities of compounds containing active hydrogen atoms so that the uncontrollable secondary reactions (by which stability of the NCO-content is adversely affected) can be avoided.

DESCRIPTION OF THE INVENTION

According to the invention, this object is achieved by the polyisocyanate mixtures according to the invention and by the process of their manufacture.

The present invention relates to polyisocyanate mixtures which are liquid and stable in storage at room temperature and which have an isocyanate content of from 36.5 to 45% by weight, characterized in that they consist essentially of a mixture of (a) from 25 to 70 parts by weight of a mixture having an NCO-content of from 22 to 36% by weight of (i) isocyanurate-group-containing trimers of 2,4-diisocyanatotoluene with (ii) 2,4-diisocyanatotoluene and (b) from 30 to 75 parts by weight of unmodified 2,4- and/or 2,6-diisocyanatotoluene.

The present invention also relates to a process for producing the new polyisocyanate mixtures comprising mixing (a) from 25 to 70 parts by weight of a partly trimerized 2,4-diisocyanatotoluene having an NCO-group content of 22 to 36% by weight, which has been obtained by trimerizing some of the isocyanate groups in 2,4-diisocyanatotoluene in the presence of a trimerization catalyst, with (b) from 30 to 75 parts by weight of 2,4- and/or 2,6-diisocyanatotoluene in such a way that a polyisocyanate mixture having an NCO-content of from 36.5 to 45% by weight is obtained.

The present invention also relates to the use of the new polyisocyanate mixtures as a component in the production of polyurethane plastics by the isocyanate polyaddition process.

It is possible by the process according to the invention to produce isocyanaurate-modified diisocyanatotoluene which may be stored as a homogeneous liquid at room temperature, the content in the mixtures of any compounds containing active hydrogen attached to nitrogen, expressed as —NH— (molecular weight=15) being kept below 0.5% by weight. In the context of the invention, compounds containing active hydrogen attached to nitrogen are understood to be any compounds which contain isocyanate-reactive HN-groups, particularly any ureas, acyl ureas, urethanes and/or allophanates containing HN-bonds, of the type used as additives in the processes described in the above-mentioned prior art or of the type formed as secondary products through the use of alcohols in the processes described in the above-mentioned prior art.

In the process according to the invention, only the technically pure, homogeneous isomer, 2,4-diisocyanatotoluene, i.e. the isomer having a purity of at least 95% by weight and preferably of at least 98% by weight, is used as starting material for the trimerization reaction because it is only on this condition that liquids storable at room temperature are obtained as the products of the process according to the invention. The fact that the products obtained where the 80:20- or 65:35-mixtures of 2,4- and 2,6-diisocyanatotoluene are used, are not stable in storage is surprising insofar as, theoretically, only 4 different isomeric monoisocyanurates can occur in the trimerization of 2,4-diisocyanatotoluene, namely:

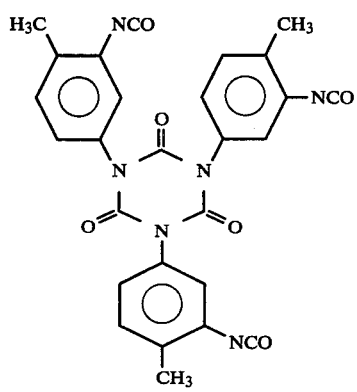

I

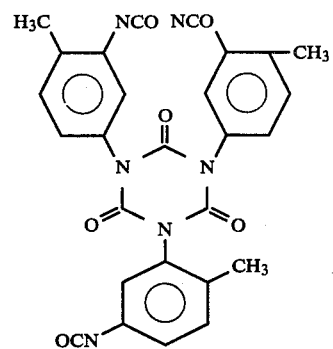

II

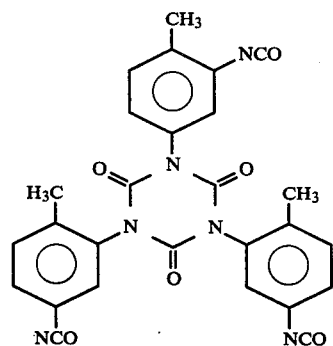

III

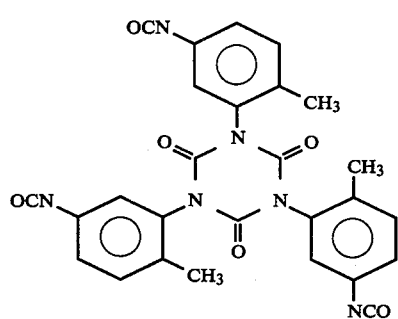

IV

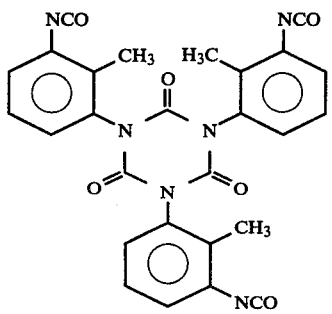

V

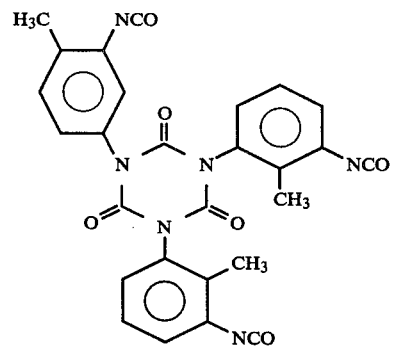

VI

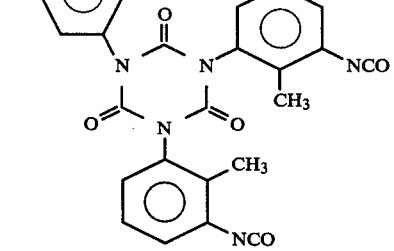

VII

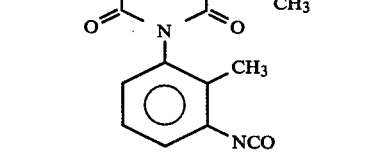

VIII

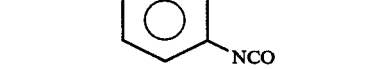

IX

By contrast, where mixtures of 2,4- and 2,6-diisocyanatotoluene are used, types V to X occur in addition to the already mentioned types I to IV, thereby increasing polymolecularity so that stability in storage would be expected to be improved. Surprisingly, the findings on which the present invention is based do not in any way confirm these theoretical expectations.

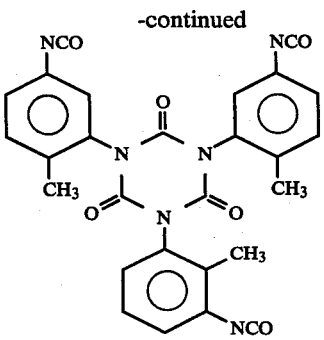

X

In principle, the process according to the invention may be carried out with any conventional trimerization catalysts, although the complexes of alkali metal compounds described in published European patent application Nos. 0056158 and 0056159 are preferably used as the trimerization catalysts. The potassium acetate complexed with open-chain or cyclic polyethylene oxide polyethers in accordance with the published European patent application just mentioned is particularly preferred.

The process according to the invention is generally carried out by subjecting from 25 to 70 parts by weight of 2,4-diisocyanatotoluene to a trimerization reaction until the NCO-content has fallen from 48.25% by weight to 36–22% by weight. This corresponds to a degree of trimerization of approximately 25 to 55% (degree of trimerization=percentage of the isocyanate groups present in the starting diisocyanate which react through trimerization). After the required degree of trimerization has been reached, the catalyst is preferably deactivated and the resulting mixture diluted with from 75 to 30 parts by weight of 2,4-diisocyanatotoluene, 2,6-diisocyanatotoluene or mixtures of these isomers and preferably with the 80:20-mixture thereof, preferably after or during the addition of the catalyst poison, to such an extent that a mixture having an NCO-content of from 36.5 to 45% by weight is obtained. Clear solutions, stable in storage at room temperature, of isocyanurate-group-containing polyisocyanate based on 2,4-diisocyanatotoluene in excess diisocyanatotoluene are obtainable in this way. Even where the trimerization reaction is carried out up to a degree of trimerization of from 50 to 55%, the reaction mixture is still a mixture of trimers of 2,4-diisocyanatotoluene with free 2,4-diisocyanatotoluene because not only monoisocyanurates corresponding to the above formulae, but also "polyisocyanaurates", i.e. isocyanate-group-containing compounds containing more than one isocyanurate ring in the molecule, are formed during the trimerization reaction so that, for example for a degree of trimerization of 55%, the reaction mixture still contains approximately 15% by weight of free 2,4-diisocyanatotoluene. This means that the above-mentioned NCO-content of component (a) of from 22 to 36% corresponds to a content of free 2,4-diisocyanatotoluene of from about 15 to about 65% by weight.

To carry out the trimerization reaction according to the invention, the 2,4-diisocyanatotoluene is initially introduced into the reaction vessel generally at 20° to 120° C. and preferably at 40° to 80° C., followed by the addition of from 5 to 50 ppm and preferably from 10 to 30 ppm of the catalyst (for example potassium acetate complexed with an equimolar quantity of a polyethylene glycol having an average molecular weight of 370). The catalyst is generally used in such a quantity that the reaction temperature rises slowly to 85°–160° C., preferably to 100°–140° C. and, more preferably, to 110°–130° C. On reaching this optimal reaction temperature, the reaction mixture is kept at that temperature by external heating or cooling and the reaction left to continue until the required NCO-content is reached. The trimerization reaction is then stopped, preferably by the addition of a catalyst poison in an at least equimolar quantity to the potassium acetate.

Suitable catalyst poisons include, for example, acid chlorides, such as acetyl chloride, benzoyl chloride, or carbamic acid chlorides or such acids as phosphoric acid, hydrochloric acid or p-toluene sulfonic acid.

Mixing with the second component of the mixtures according to the invention, i.e. with the 2,4- and/or 2,6-diisocyanatotoluene, is preferably carried out immediately after completion of the trimerization reaction, i.e. at temperatures in the range from 85°–160° C. and preferably from 100° to 140° C., the mixture as a whole generally cooling to around 80° to 100° C. The mixture is then stirred at that temperature until a clear solution has formed. It is also possible to terminate the trimerization reaction and to dilute the reaction mixture with unmodified diisocyanatotoluene at one and the same time by adding a mixture of diisocyanatotoluene and catalyst poison to the trimerization reaction mixture. Termination of the trimerization reaction immediately after dilution is also possible in principle, although less preferred. The trimerization reaction may also be carried out without using a catalyst poison. This is possible when the trimerization catalyst is used in the subequivalent quantity, based on the hydrolyzable chlorine content of the 2,4-diisocyanatotoluene used, so that the catalyst is "automatically" deactivated during the trimerization reaction. The trimerization reaction may of course also be carried out without using catalyst poisons in cases where the known trimerization catalysts decomposing under the effect of heat are used.

The polyisocyanate mixtures according to the invention are eminently suitable for the production of polyurethane plastics and, more particularly, for the production of flexible, elastic polyurethane foams having an improved compression set value (compared with the use of unmodified diisocyanatotoluene) and an improved compression hardness value, increased foaming safety being guaranteed by the outstanding NCO-value-stability of the mixtures.

Comparison Examples 1 to 3 below show that, where a technical 80:20-mixture of 2,4- and 2,6-diisocyanatotoluene is used for the trimerization reaction, the product obtained is not stable in storage irrespective of the degree of trimerization:

EXAMPLE 1 (Comparison)

400 g of a technical grade 80:20-mixture of 2,4- and 2,6-diisocyanatotoluene are initially introduced at 50° C. into a 2 liter flask equipped with a stirrer, nitrogen inlet, thermometer and reflux condenser, followed by the addition of 1.2 ml of a 0.1-molar solution of potassium acetate in polyethylene glycol (average molecular weight: 370). After 12 minutes, the internal temperature has risen to 105° C. and the NCO-content has fallen to 38.4%. The trimerization reaction is terminated by stirring in 600 g of an 80:20 mixture of 2,4- and 2,6-tolylene diisocyanate to which 0.13 mMole of benzoyl chloride has been added. The mixture is then stirred at 90° to 100° C. until all the trimer has clearly dissolved. The end product has an NCO-content of 44.3%.

EXAMPLE 2 (Comparison)

As in Example 1, the addition of 1.3 ml of a 0.1-molar solution of potassium acetate/18-crown-6 (1:1) in diethylene glycol monomethylether ("18-crown-6"=1,4,7,10,13,16-hexaoxycyclooctadecane (R. N. Greene, Tetrahedron Lett. 18, (1972), pages 1793–1796) to 400 g of an 80:20 mixture of 2,4- and 2,6-diisocyanatotoluene produces an internal temperature of 99° C. after 15 minutes and an NCO-content of 28.9% at which the reaction is terminated by the addition of 600 g of an 80:20 mixture of 2,4- and 2,6-tolylene diisocyanate to which 1.4 mMole of benzoyl chloride has been added. The end product has an NCO-content of 40.5%.

EXAMPLE 3 (Comparison)

As in Example 1, the addition of 1.4 ml of a 0.1-molar solution of potassium acetate/18-crown-6 (1:1) in diethylene glycol monomethyl ether to 400 g of an 80:20 mixture of 2,4- and 2,6-tolylene diisocyanate produces an internal temperature of 135° C. after 9 minutes and an NCO-content of 22.4% at which the reaction is terminated by the addition of 600 g of an 80:20 mixture of 2,4- and 2,6-tolylene diisocyanate to which 1.5 mMoles of benzoyl chloride have been added. The end product has an NCO-content of 37.9%.

The product of Comparison Example 1 (degree of trimerization [DT]=20.4%) begins to precipitate a crystalline deposit after 11 days, the product of Comparison Example 2 (DT=40%) after 14 days and the product of Comparison Example 2 (DT=53.6%) after 16 days. If all three products are left to crystallize completely at T=−20° C. and then remelted at 30° C., all three remain cloudy and a crystalline deposit is precipitated after 2 to 3 days.

General Procedure for Examples 4–10

According to the Invention (see Table 1)

In a stirrer-equipped apparatus provided with a thermometer, reflux condenser and nitrogen inlet, the indicated quantity of 2,4-diisocyanato-toluene (2,4-TDI) is initially introduced at the starting temperature ($T_s$) indicated, followed by addition of the corresponding catalyst solution:

A=0.1 molar solution of potassium acetate/18-crown-6 in diethylene glycol monomethylether
B=0.025 molar solution of potassium acetate/-polyethylene glycol (av. MW=370) (1:5) in diethylene glycol monomethyl ether
C=0.025 molar solution of potassium acetate in polyethylene glycol (av. MW=370).

The reaction mixture is then stirred until the required degree of trimerization (DT) is reached. The trimerization reaction is stopped immediately, if the temperature rises above 130° C., or, in the event of a slow increase in temperature to 100°–130° C., the reaction mixture is kept by additional heating at the maximum temperature reached ($T_h$). Cooling to temperatures below 100° C. should be avoided because, with an NCO-content of <32%, satisfactory mixing is not guaranteed due to an excessive increase in viscosity. When the NCO-content has fallen to the necessary level (reaction time $t_R$), the trimerization reaction is stopped by addition of the indicated quantity of an 80:20-mixture of 2,4- and 2,6-tolylene diisocyanate (80:20 2,4-:2,6-TDI) to which benzoyl chloride has been added in a quantity equivalent to the potassium acetate used and the mixture stirred at 90° to 100° C. until all the trimer has clearly dissolved. The data of the products obtained in Examples 4 to 9 are shown in the following Table.

TABLE

| | Quantity of 2,4-TDI (g) | $T_s$ (°C.) | Catalyst Type Sol. (ml) | $T_h$ (°C.) | $t_R$ (min.) | NCO (%) | Quantity of 80/20-2,4/2,6-TDI (g) | End Product NCO (%) |
|---|---|---|---|---|---|---|---|---|
| Example 4 | 800 | 50 | C; 3.4 | 130 | 2 | 33.1 | 1200 | 42.2 |
| Example 5 | 800 | 80 | C; 3.7 | 121 | 115 | 29.1 | 1200 | 40.6 |
| Example 6 | 800 | 70 | B; 5.8 | 105 | 70 | 30.4 | 1200 | 41.1 |
| Example 7 | 100 | 50 | A; 0.3 | 96 | 10 | 35.2 | 150 | 43 |
| Example 8 | 400 | 50 | A; 1.2 | 159 | 4 | 23.3 | 600 | 38.3 |
| Example 9 | 2000 | 50 | C; 6.2 | 130 | 30 | 29.6 | 3000 | 40.8 |

The products of Examples 4–9 according to the invention remain stable in storage for more than 6 months. Product completely crystallized by cooling to T=−20° C. completely remelts at temperatures in the range from 20° to 40° C. to form a clear solution.

EXAMPLE 10 (Application Example)

A mixture consisting of 100 parts by weight of a polyetherpolyol having an OH-number of 28 obtained by propoxylation of trimethylol propane with subsequent ethoxylation of the propoxylation product (PO/EO-weight ratio=87:13)
3.2 parts by weight of water
0.2 part by weight of triethylene diamine
0.1 part by weight of bis-(dimethylaminoethyl)-ether
1.6 parts by weight of diisopropanolamine
1.0 part by weight of diethanolamine
0.15 part by weight of a commercial chlorine-containing polysiloxane stabilizer (stabilizer KS 53 of Bayer AG, Leverkusen).
3.9 parts by weight of glycerol is intensively mixed with 65.5 parts by weight of an isocyanate produced in accordance with Example 5 and the resulting mixture foamed in an open mold. A non-shrinking readily expanding and highly elastic foam having the following mechanical properties is formed:

| | |
|---|---|
| Gross density (kg/m³) | 38 |
| Tensile strength (kPa) | 95 |
| Breaking elongation (%) | 120 |
| Compression hardness (kPa) at 40% deformation | 4.6 |
| Compression set (%) at 90% compression | 7.5 |

What is claimed is:

1. A polyisocyanate mixture which is liquid and storable at room temperature and which has an isocyanate content of from 36.5 to 45% by weight, consisting essentially of
   (a) from 25 to 70 parts by weight of a mixture having an NCO-content of from 22 to 36% by weight of (i) isocyanurate-group-containing trimers of 2,4-diisocyanatotoluene and (ii) 2,4-diisocyanatotoluene and
   (b) from 30 to 75 parts by weight of 2,4- and/or 2,6-diisocyanatotoluene.

2. The polyisocyanate mixture of claim 1, characterized in that it contains less than 0.5% by weight of compounds containing active hydrogen atoms attached to nitrogen, expressed as —NH—.

3. The polyisocyanate mixture of claim 1 wherein said mixture having an NCO-content of from 22 to 36% by weight is produced by trimerizing 2,4-diisocyanatotoluene to a degree of trimerization of about 25 to 55%.

4. A process for producing a polyisocyanate mixture which is liquid and storable at room temperature comprising mixing
   (a) from 25 to 70 parts by weight of a partly trimerized 2,4-diisocyanatotoluene with an NCO-content of from 22 to 36% by weight which has been produced by trimerizing some of the isocyanate groups in 2,4-diisocyanatotoluene in the presence of a trimerization catalyst, with
   (b) from 30 to 75 parts by weight of 2,4- and/or 2,6-diisocyanato-toluene in such a way that a polyisocyanate mixture having an NCO-content of from 36.5 to 45% by weight is obtained.

5. The process of claim 4, characterized in that potassium acetate complexed with open-chain or cyclic polyethylene oxide polyethers is used as the trimerization catalyst.

6. In a method of manufacturing a polyurethane and/or polyurea product by reacting an isocyanate with an active hydrogen containing material, the improvement wherein the isocyanate used is
   (a) from 25 to 70 parts by weight of a mixture having an NCO-content of from 22 to 36% by weight of (i) isocyanurate-group-containing trimers of 2,4-diisocyanatotoluene and (ii) 2,4-diisocyanatotoluene and
   (b) from 30 to 75 parts by weight of 2,4- and/or 2,6-diisocyanatotoluene.

* * * * *

UNITED STATES PATENT AND TRADEMARK OFFICE
CERTIFICATE OF CORRECTION

PATENT NO. : 4,456,709
DATED : June 26, 1984
INVENTOR(S) : Roland Richter, Hanns Hettel, Hanns P. Müller It is certified that error appears in the above—identified patent and that said Letters Patent is hereby corrected as shown below:

At column 1, line 21, "U.S. Pat. No. 4,243,765" should read --U.S. Pat. No. 4,243,756--.

Please add --Great Britain Pat. No. 1,381,511-- to the list of Foreign Patent Documents.

At column 5, line 23, "application" should read --applications--.

Signed and Sealed this

Fifth Day of August 1986

[SEAL]

Attest:

DONALD J. QUIGG

Attesting Officer     Commissioner of Patents and Trademarks